(12) United States Patent  
Hedmann et al.

(10) Patent No.: US 8,992,461 B2
(45) Date of Patent: Mar. 31, 2015

(54) APPARATUS FOR PERITONEAL DIALYSIS

(75) Inventors: Frank Hedmann, Volkach (DE); Stephan Klatte, Nienburg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 940 days.

(21) Appl. No.: 12/493,814

(22) Filed: Jun. 29, 2009

(65) Prior Publication Data
US 2010/0004590 A1 Jan. 7, 2010

(30) Foreign Application Priority Data

Jul. 4, 2008 (DE) .......................... 10 2008 031 662

(51) Int. Cl.
*A61M 1/00* (2006.01)
*A61M 1/28* (2006.01)

(52) U.S. Cl.
CPC .......... *A61M 1/28* (2013.01); *A61M 2205/3344* (2013.01)
USPC .................................. 604/29; 604/28; 604/30

(58) Field of Classification Search
CPC .................. A61M 1/28; A61M 2205/3344
USPC ........................................ 604/28–30
See application file for complete search history.

(56) References Cited

U.S. PATENT DOCUMENTS

| 4,678,566 | A | * | 7/1987 | Watanabe et al. ............. 210/143 |
| 5,004,459 | A |   | 4/1991 | Peabody |
| 5,141,493 | A |   | 8/1992 | Jacobsen et al. |
| 5,250,041 | A | * | 10/1993 | Folden et al. ................. 604/284 |
| 5,437,683 | A | * | 8/1995 | Neumann et al. ............. 606/151 |
| 5,542,919 | A |   | 8/1996 | Simon et al. |
| 5,609,572 | A | * | 3/1997 | Lang ................................ 604/22 |
| 5,641,405 | A |   | 6/1997 | Keshaviah et al. |
| 5,938,634 | A |   | 8/1999 | Packard |
| 6,074,359 | A | * | 6/2000 | Keshaviah et al. ............... 604/29 |
| 6,228,047 | B1 |   | 5/2001 | Dadson |
| 6,497,676 | B1 |   | 12/2002 | Childers et al. |
| 6,542,761 | B1 |   | 4/2003 | Jahn et al. |
| 6,743,201 | B1 |   | 6/2004 | Dönig et al. |
| 6,929,751 | B2 |   | 8/2005 | Bowman et al. |
| 7,083,719 | B2 |   | 8/2006 | Bowman et al. |
| 2002/0120227 | A1 | * | 8/2002 | Childers et al. ................. 604/29 |
| 2004/0019312 | A1 |   | 1/2004 | Childers |
| 2007/0106247 | A1 |   | 5/2007 | Burnett |
| 2009/0012447 | A1 | * | 1/2009 | Huitt et al. ...................... 604/28 |

FOREIGN PATENT DOCUMENTS

| CN | 2748034 Y | 12/2005 |
| DE | 69215123  | 6/1997  |

(Continued)

OTHER PUBLICATIONS

"*Bizarre Effects Occur in Certain materials at Very Low Temperatures.*" Superconductivity and Superfluidity. Ph. 09 Outlook. [retrieved on Apr. 6, 2009]. Retrieved from http://leifi.physik.uni-muenchen.de/web_ph09/umwelt_technik/02supraleit/supraleit.h. (Translated version), pp. 1-3.

*Primary Examiner* — Edelmira Bosques
(74) *Attorney, Agent, or Firm* — Fish & Richardson P.C.

(57) ABSTRACT

The invention relates to an apparatus for peritoneal dialysis having a device for the regular dispensing and reuptake of dialysate. The device has a pressure measuring device for the measurement of intraperitoneal pressure.

18 Claims, 2 Drawing Sheets

(56) References Cited

FOREIGN PATENT DOCUMENTS

| DE | 69610896 | 4/2005 |
|---|---|---|
| EP | 0402505 | 12/1990 |
| EP | 0498382 | 11/1996 |
| EP | 0749328 | 4/2003 |
| EP | 1253954 | 6/2006 |
| WO | WO 9709074 | 3/1997 |
| WO | WO 99/06082 | 2/1999 |
| WO | WO9906082 A1 | 2/1999 |
| WO | WO 01/58509 | 8/2001 |
| WO | WO 2005/035023 | 4/2005 |

\* cited by examiner

APPARATUS FOR PERITONEAL DIALYSIS

CROSS REFERENCE TO RELATED APPLICATION

This application claims priority under 35 U.S.C. §119(a) to German Patent Application No. 10 2008 031 662.8, filed Jul. 4, 2008, the entire contents of which are hereby incorporated by reference.

TECHNICAL FIELD

The invention relates to an apparatus for peritoneal dialysis having a device for the regular dispensing and reuptake of dialysate. The invention further relates to a device and method for the measurement of intraperitoneal pressure.

BACKGROUND

Peritoneal dialysis is a variant of artificial blood cleansing. The patient's peritoneum, which is well supplied with blood, is used as the body's own filter membrane in peritoneal dialysis. During peritoneal dialysis, dialysate is introduced into the abdominal cavity via a catheter. Urine components are removed from the blood in accordance with the osmosis principle and enter the abdominal cavity. After some hours, the dialysate with the urine components is drained from the abdominal cavity.

There are generally different options for carrying out peritoneal dialysis. In continuous ambulatory peritoneal dialysis (CAPD), the patients themselves replace the dialysate approximately four to five times a day. In automated peritoneal dialysis (APD), an apparatus, the so-called cycler, takes over the automatic bag change overnight so that the patient is still independent during the day.

In automated peritoneal dialysis in which the abdominal cavity is filled with the help of the aforesaid cycler, a volumetric control is usually used to ensure that no more than a maximum filling volume is dispensed to the patient. This maximum filling volume amounts, for example, to 3,500 ml in an average adult. As a rule, standardized values are used for the filling volume since the effort for an experimental determination of the filling volume individual to the patient should be avoided.

SUMMARY

It is an object of the present invention to further develop a device for peritoneal dialysis such that the volume of the respective dialysate to be dispensed can be determined automatically. A corresponding measuring method is also provided.

This object is solved in accordance with the invention in that, with a generic apparatus for peritoneal dialysis, a pressure measuring device is provided for the measurement of the intraperitoneal pressure.

The intraperitoneal pressure is understood to be the internal pressure of the peritoneum which results from the abdominal cavity being filled with dialysate and a counter pressure on the peritoneum. The intraperitoneal pressure can be used to determine the ideal amount of filling for the individual patient. The provision of the pressure measuring device permits a pressure-controlled filling of the abdominal cavity while utilizing the individually present volume.

Accordingly, the static pressure and/or dynamic pressure during filling can be measured via the pressure device.

The pressure measuring device advantageously has a double lumen line or two parallel lines in addition to the pressure measuring sensors. In a particularly advantageous embodiment of the invention, one of the two lines is closed via a filter with respect to the environment such that the ambient pressure can be transmitted to the pressure sensor on the apparatus side.

The double lumen line is particularly advantageously made as a disposable so that it can be replaced after every treatment.

In accordance with a preferred embodiment of the invention, the apparatus includes a control unit by means of which the dispensing by the machine of the dialysate can be controlled based on the pressure values determined.

In this respect, a control can run on the control unit on the carrying out of a dynamic pressure measurement such that the pressure of the patient line is monitored, with this measured pressure being compensated by the dynamic properties and being reduced by the pressure of the second line measuring the ambient pressure. In this measurement, the flow resistances of the line and of the catheter are known so that these values can be compensated as dynamic properties during the flow rate compensation.

Alternatively, the pressure of the patient line can be monitored in the form of a static measurement at different filling levels. In such cases, the pressure of the patient line is monitored cyclically by means of the pressure measuring device, and the measured pressure is reduced by the pressure of the second line measuring the ambient pressure.

It is particularly advantageous to exclude various error sources related to the use of the apparatus. If, for example, an unexpected intraperitoneal pressure or pressure increase is recorded, this can indicate different error sources. The abdominal cavity of the patient may, for example, not have been completely emptied before the filling procedure. Furthermore, a treatment program might have been incorrectly selected for an adult in which a high filling volume has to be dispensed, although it is actually a child that is connected to the machine.

These errors can be reliably prevented on the use of the apparatus in accordance with the invention.

DESCRIPTION OF DRAWINGS

Further features, details and advantages of the invention will be explained in more detail with reference to an embodiment shown in the drawing. There are shown.

DETAILED DESCRIPTION

Figure 1:
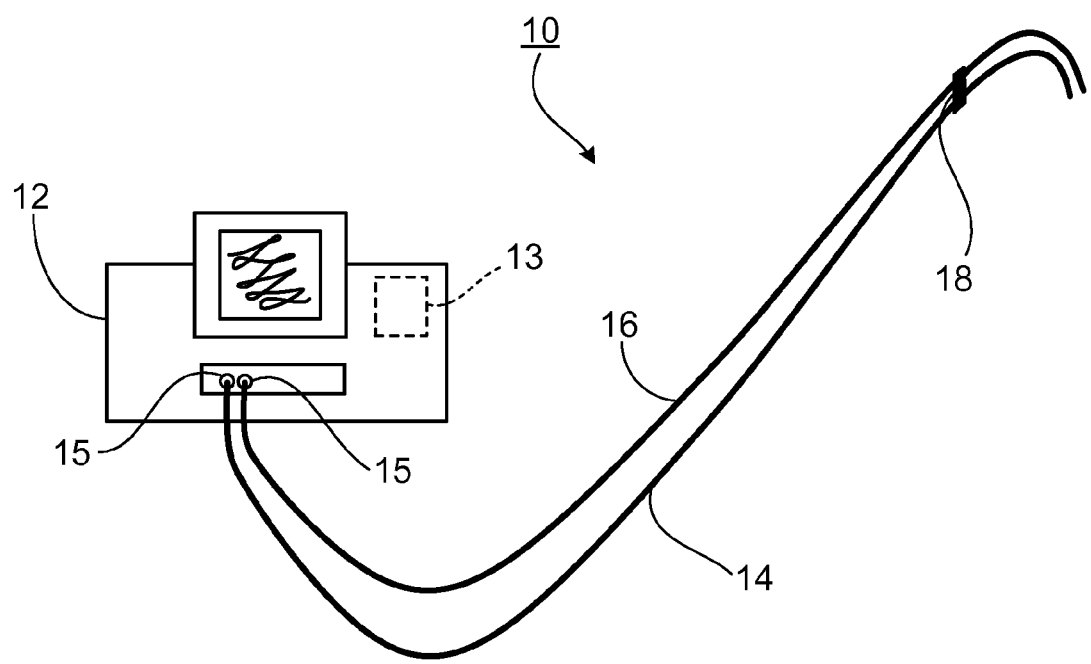
FIG. 1: an embodiment of a peritoneal dialysis apparatus in accordance with the invention in a purely schematic representation.

The apparatus 10 for peritoneal dialysis in accordance with the embodiment shown in FIG. 1 has a so-called cycler 12 whose design is known per se and which fills and empties the patient's abdominal cavity automatically. A patient line 14 defining a fluid passageway adjoins the cycler 12. A second line 16 defining a fluid passageway is made as a measuring line beside the patient line 14 via which the dialysate is transported. The ends of the lines 14 and 16 at the sides of the cyclers are each coupled with a pressure sensor 15 such that the respective pressure prevailing in the line can be measured.

It is a requirement for the measurement of the intraperitoneal pressure (i.e., the internal pressure of the peritoneum) that the second line 16 as the measurement line is completely filled with dialysate and ends at the same level as the end of the patient line, and that the measurement line communicates with the environment at its free end via a filter device (not shown) so that ambient pressure is applied to the free end of the line 16.

To ensure that the free end of the second line 16 is at the same level as the patient line 14, a mechanical connection 18 is provided close to the end of the lines 14 and 16. The mechanical connection 18 can be a clip, for example.

Figure 2:
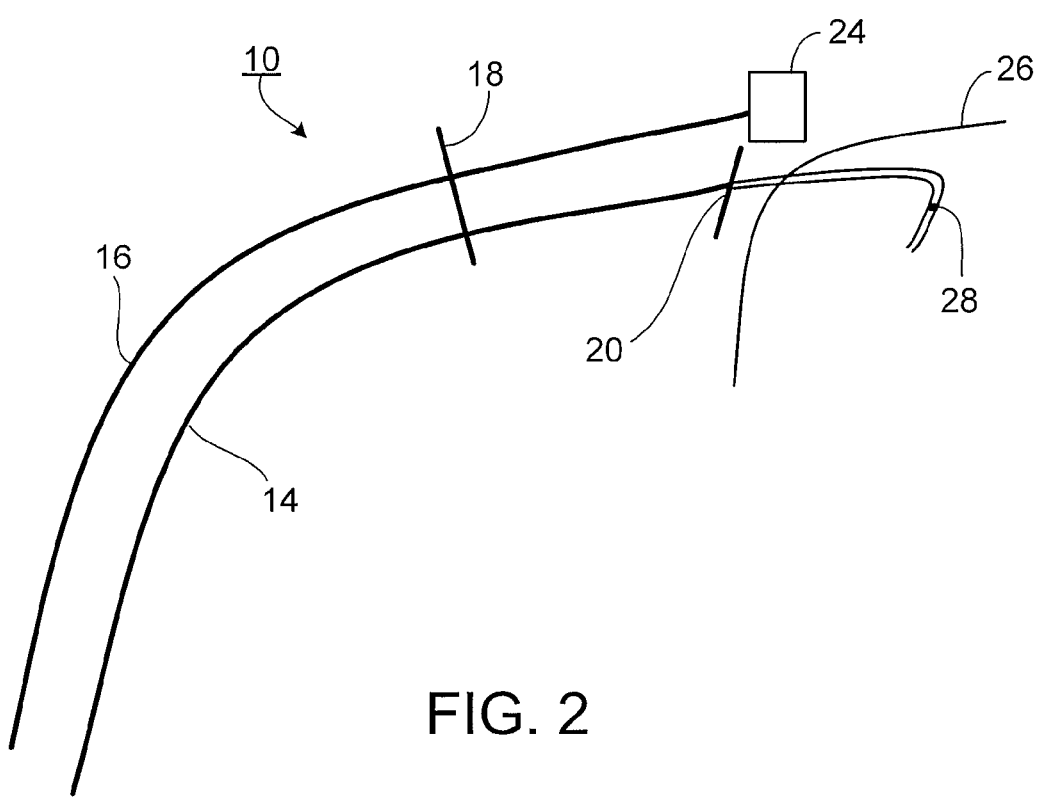
FIG. 2: a detailed view of lines of the peritoneal dialysis apparatus of FIG. 1.

As shown in FIG. 2, the free end of the measuring line 16 ends in a filter 24 which is liquid-tight and air-permeable. The patient line 14 is connected via a connector 20 to the peritoneum by a catheter 28 passing trough the abdominal wall 26 of the patient.

The cycler 12 has a control unit 13 by means of which the dispensing by the machine of the dialysate can be controlled based on the pressure values determined. The control runs in the control unit 13 with a cyclic measurement such that initially only the purely static pressure is measured via the pressure sensor arranged at the second line 16.

The intraperitoneal pressure is measured in addition to the static pressure at the other pressure sensor which is connected to the patient line 14. The intraperitoneal pressure can thus be calculated in this static measurement in that the static pressure measured using the second line 16 is deducted.

For pressure measurements made during operation (i.e., dynamic pressure measurements), the so-called dynamic values must additionally be included in the calculation. They result on the line and the catheter being flowed through by the flow resistances in the line and the catheter. The so-called flow rate compensation can be determined for the present system and can thus be considered in a calculatory manner in the control unit on a dynamic measurement of the pressure.

The abdominal cavity of the patient is filled in a pressure-controlled manner using the apparatus in accordance with the invention in accordance with the pressure values.

The invention claimed is:

1. A peritoneal dialysis apparatus, comprising:
a first fluid passageway that can be placed in fluid communication with a peritoneal cavity of a patient during peritoneal dialysis;
a second fluid passageway including a free end that can be placed in fluid communication with atmospheric air during peritoneal dialysis;
a first pressure sensor configured to measure pressure in the first fluid passageway;
a second pressure sensor configured to measure pressure in the second fluid passageway; and
a filter disposed at the free end and that closes the second fluid passageway, the filter being liquid impermeable and air permeable such that ambient pressure is applied to the free end of the second fluid passageway; and
a control unit configured to determine intraperitoneal pressure based on pressures measured by the first and second pressure sensors when the first fluid passageway is in fluid communication with the peritoneal cavity of the patient and the second fluid passageway is in fluid communication with atmospheric air, wherein the control unit is configured to determine the intraperitoneal pressure by deducting static pressure detected in the second fluid passageway from the pressure in the first fluid passageway.

2. The apparatus of claim 1, wherein the control unit is configured to control the delivery of dialysate to the peritoneal cavity of the patient via the first fluid passageway based on the determined intraperitoneal pressure.

3. The apparatus of claim 1, wherein the first and second fluid passageways are formed by a single fluid line.

4. The apparatus of claim 3, wherein the single fluid line is disposable.

5. The apparatus of claim 1, wherein the pressure in the first fluid passageway is continuously measured.

6. The apparatus of claim 1, wherein the pressure in the first fluid passageway is cyclically measured.

7. The apparatus of claim 1, wherein the pressure in the first fluid passageway is measured during operation, and the intraperitoneal pressure is further determined by accounting for flow resistance in the first fluid passageway.

8. The apparatus of claim 1, wherein the first fluid passageway is formed by a first fluid line, and the second fluid passageway is formed by a second fluid line.

9. The apparatus of claim 8, wherein the first and second fluid lines are parallel to one another.

10. The apparatus of claim 9, wherein the first and second fluid lines are connected to one another by a mechanical connector.

11. The apparatus of claim 8, wherein the second fluid line is filled with dialysate and terminates at substantially the same level as the first fluid line.

12. The apparatus of claim 8, wherein the first and second fluid lines are disposable.

13. A peritoneal dialysis method, comprising:
measuring a first pressure in a first fluid passageway that is in fluid communication with a peritoneal cavity of a patient;
measuring a second pressure in a second fluid passageway that is in fluid communication with atmospheric air; and
determining intraperitoneal pressure based on the first and second measured pressures,
wherein the second fluid passageway is formed in a fluid line having a free end, and a filter is disposed at the free end and closes the second fluid passageway, the filter being liquid impermeable and air permeable such that ambient pressure is applied to the free end of the second fluid passageway,
wherein the measured second pressure is static pressure due to fluid filling the second fluid passageway while ambient air pressure is applied to the free end of the second fluid passageway, and the intraperitoneal pressure is determined by deducting the static pressure from the first pressure.

14. The method of claim 13, further comprising controlling the delivery of dialysate to the peritoneal cavity of the patient via the first fluid passageway based on the determined intraperitoneal pressure.

15. The method of claim 13, wherein the first pressure is continuously measured.

16. The method of claim 13, wherein the first pressure is cyclically measured.

17. The method of claim 13, wherein the first pressure is measured during operation, and the intraperitoneal pressure is further determined by accounting for flow resistance in the first fluid passageway.

18. The method of claim 13, wherein the second fluid passageway is filled with dialysate and terminates at substantially the same level as the first fluid passageway.

* * * * *